United States Patent
Scruggs et al.

(10) Patent No.: US 9,907,587 B2
(45) Date of Patent: Mar. 6, 2018

(54) FIXATION IMPLANT DEVICES, SYSTEMS, KITS, AND METHODS

(71) Applicant: Wright Medical Technology, Inc., Memphis, TN (US)

(72) Inventors: Phillip Charles Scruggs, Memphis, TN (US); Timothy Michael O'Kane, Munford, TN (US); Brian Thoren, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 76 days.

(21) Appl. No.: 14/421,380

(22) PCT Filed: Jan. 28, 2015

(86) PCT No.: PCT/US2015/013256
§ 371 (c)(1),
(2) Date: Feb. 12, 2015

(87) PCT Pub. No.: WO2016/122484
PCT Pub. Date: Aug. 4, 2016

(65) Prior Publication Data
US 2016/0338746 A1 Nov. 24, 2016

(51) Int. Cl.
*A61F 2/42* (2006.01)
*A61B 17/72* (2006.01)
(Continued)

(52) U.S. Cl.
CPC ........ *A61B 17/725* (2013.01); *A61B 17/7291* (2013.01); *A61B 17/60* (2013.01); *A61B 2017/681* (2013.01)

(58) Field of Classification Search
CPC ........ A61F 2/42; A61F 2/4225; A61F 2/4241; A61F 2002/4212; A61F 2002/4215;
(Continued)

(56) References Cited

U.S. PATENT DOCUMENTS 4,943,293 A * 7/1990 Lee, Jr. ............... A61B 17/60
128/888
5,658,287 A 8/1997 Hoffman et al.
(Continued)

FOREIGN PATENT DOCUMENTS

EP 0 787 467 A1 8/1997
EP 2668929 A1 12/2013
(Continued)

OTHER PUBLICATIONS

International Search Report and Written Opinion issued for International Application No. PCT/US2015/013256, Feb. 16, 2015, 8 pages.

(Continued)

*Primary Examiner* — Lynnsy Summitt
(74) *Attorney, Agent, or Firm* — Duane Morris LLP

(57) ABSTRACT

A device includes a housing and a locking assembly disposed within a spaced defined by the housing. The housing defines a hole that extends through the housing. The locking assembly is configured to allow the device to slide along an elongate orthopedic device in a first direction and to hinder the device from sliding along an elongate orthopedic device in a second direction that is opposite the first direction.

15 Claims, 9 Drawing Sheets

(51) Int. Cl.
*A61B 17/60* (2006.01)
*A61B 17/68* (2006.01)

(58) Field of Classification Search
CPC ........ A61F 2002/422; A61F 2002/4228; A61F 2002/423; A61F 2002/4238; A61F 2002/4243; A61F 2002/4246; A61F 2002/4248; A61F 2002/4251; A61F 2002/4253; A61B 2017/681; A61B 17/683; A61B 17/685; A61B 17/686
See application file for complete search history.

(56) References Cited

U.S. PATENT DOCUMENTS

| | | | | |
|---|---|---|---|---|
| 5,989,255 | A * | 11/1999 | Pepper | A61B 17/8685 606/306 |
| 6,302,889 | B1 | 10/2001 | Keller | |
| 8,372,081 | B1 * | 2/2013 | Schafer | A61B 17/7077 606/105 |
| 2004/0153067 | A1 * | 8/2004 | Smith | A61B 17/8076 606/60 |
| 2006/0184169 | A1 * | 8/2006 | Stevens | A61B 17/62 606/54 |
| 2008/0147126 | A1 * | 6/2008 | Tipirneni | A61B 17/8869 606/300 |
| 2008/0287998 | A1 | 11/2008 | Doubler et al. | |
| 2009/0036893 | A1 | 2/2009 | Kartalian et al. | |
| 2009/0163962 | A1 | 6/2009 | Dauster et al. | |
| 2009/0306720 | A1 | 12/2009 | Doubler et al. | |
| 2010/0023061 | A1 | 1/2010 | Randol et al. | |
| 2010/0312288 | A1 | 12/2010 | Hammill, Sr. et al. | |
| 2011/0004255 | A1 | 1/2011 | Weiner et al. | |
| 2011/0082508 | A1 | 4/2011 | Reed | |
| 2011/0196370 | A1 | 8/2011 | Mikhail | |
| 2011/0301653 | A1 | 12/2011 | Reed et al. | |
| 2013/0079776 | A1 * | 3/2013 | Zwirkoski | A61B 17/68 606/62 |
| 2013/0131822 | A1 | 5/2013 | Lewis et al. | |
| 2013/0296857 | A1 * | 11/2013 | Barnett | A61B 17/6416 606/57 |
| 2014/0194907 | A1 * | 7/2014 | Bonutti | A61B 17/8866 606/151 |
| 2014/0276822 | A1 * | 9/2014 | Cresina | A61B 17/6416 606/57 |
| 2016/0038186 | A1 * | 2/2016 | Herzog | A61B 17/683 606/304 |

FOREIGN PATENT DOCUMENTS

| | | | | |
|---|---|---|---|---|
| FR | EP 0787467 A1 * | 8/1997 | ........... A61B 17/685 |
| JP | 2002-159900 A | 6/2002 | |
| JP | 2012-507355 A | 3/2012 | |
| JP | 2012-520100 A | 9/2012 | |
| JP | 2014-161726 A | 9/2014 | |
| WO | 2013/082354 A1 | 6/2013 | |
| WO | 2014/072082 A1 | 5/2014 | |

OTHER PUBLICATIONS

Office Action issued in connection with corresponding Canadian patent application No. 2,896,953, May 5, 2016, 5 pages.
Office Action issued in connection with corresponding Australian patent application No. 2015202182, Jun. 17, 2016, 6 pages.
Office Action issued for corresponding Canadian Patent Application No. 2,896,953, Feb. 15, 2017, 4 pages.

* cited by examiner

US 9,907,587 B2

FIXATION IMPLANT DEVICES, SYSTEMS, KITS, AND METHODS

CROSS REFERENCE TO RELATED APPLICATIONS

This application is a national phase entry under 35 U.S.C. § 371 of international patent application No. PCT/US2015/13256, filed Jan. 28, 2015, the entirety of which is herein incorporated by reference.

FIELD OF DISCLOSURE

The disclosed devices, systems, kits, and methods relate to orthopedic fixation. More particularly, the disclosed devices, systems, kits, and methods relate to orthopedic fixation using in combination with k-wires and other orthopedic devices.

BACKGROUND

Jurgan's balls are used frequently in the treatment of hammertoe. These conventional devices utilize a set screw to fix the Jurgan's ball at a particular location. However, setting the set screw requires the use of small instruments to tighten the set screw, which can be difficult to engage during surgery. Further, the set screw is susceptible from becoming loose over time as the patient moves about.

SUMMARY

In some embodiments, a device includes a housing and a locking assembly disposed within a spaced defined by the housing. The housing defines a hole that extends through the housing. The locking assembly is configured to allow the device to slide along an elongate orthopedic device in a first direction and to hinder the device from sliding along an elongate orthopedic device in a second direction that is opposite the first direction.

In some embodiments, a method includes inserting an elongate orthopedic device into at least one bone of a patient and sliding a first fixation device along a length of the elongate orthopedic device such that the elongate orthopedic device is received within a hole defined by a housing of the first fixation device. The first fixation device includes a locking assembly disposed within a spaced defined by the housing. The locking assembly of the first fixation device is configured to allow the first fixation device to slide along the elongate orthopedic device in a first direction and to hinder the first fixation device from sliding along the elongate orthopedic device in a second direction that is opposite the first direction.

DETAILED DESCRIPTION

Figure 1:
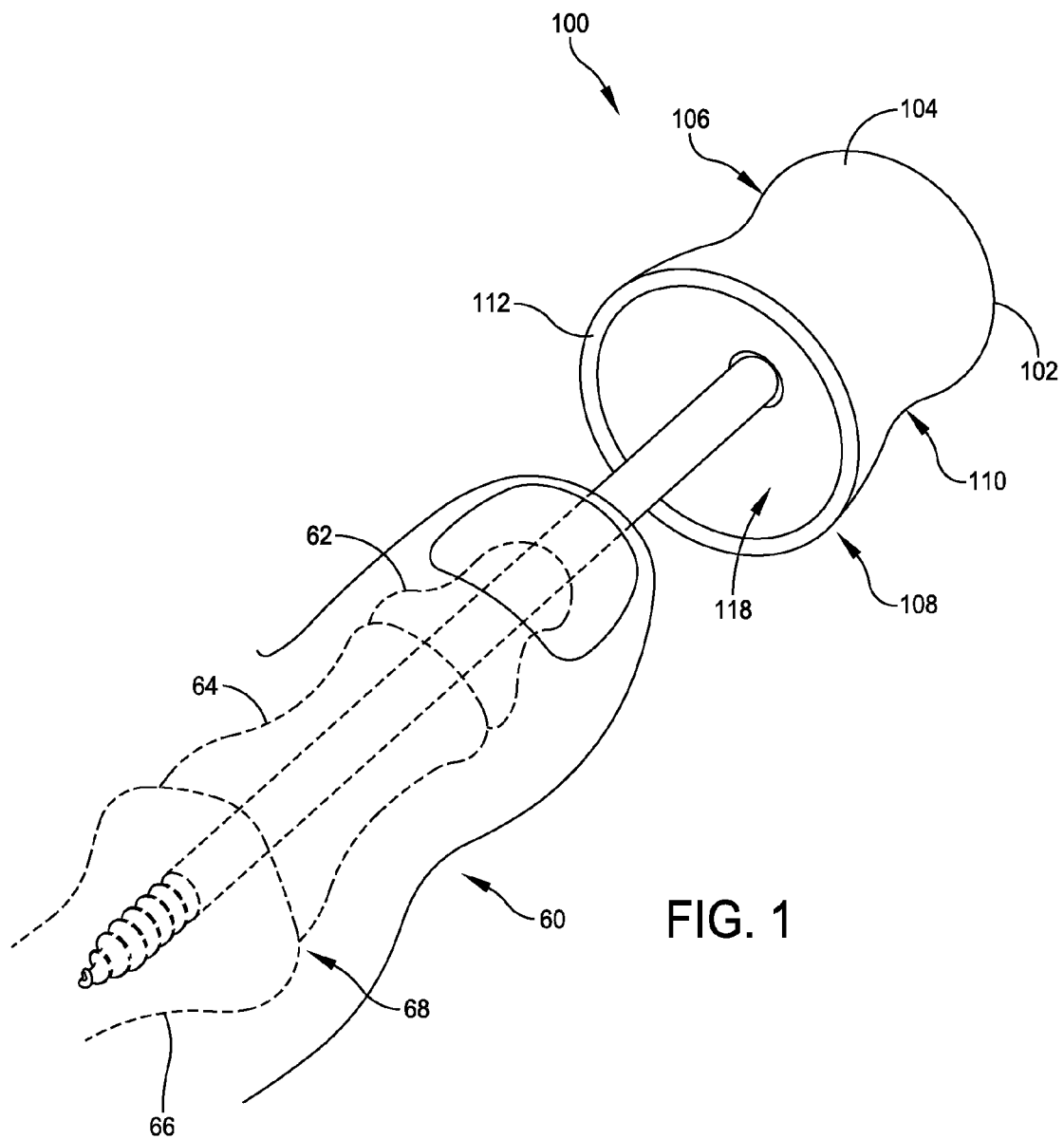
FIG. 1 is an isometric view of a fixation device being slid over an elongate orthopedic device in accordance with some embodiments.

This description of the exemplary embodiments is intended to be read in connection with the accompanying drawings, which are to be considered part of the entire written description.

The disclosed devices, systems, kits, and methods provide for locking mechanisms for use with k-wires and other orthopedic devices. In some embodiments, the disclosed systems and associated methods are used with k-wires in the treatment of hammertoe or other deformities or ailments of extremities, such as fingers and feet.

One example of a fixation device 100 is illustrated in FIGS. 1-6. As shown in FIGS. 1-6, device 100 includes a housing 102 having a body 104 having a first portion 106 and a second portion 108 that merge together at intersection 110. In some embodiments, the shape of first portion 106 is generally spherical, and the shape of second portion 108 resembles a thimble in that a hollow cylindrical wall 112 extends away from intersection 110. Body 104 can be formed from a polymeric, metal, and/or ceramic material through any suitable means including, but not limited to, injection molding or an additive manufacturing process (e.g., 3D printing). In some embodiments, body 104 is a monolith, but body 104 also can include two or more components that are joined together. For example, in embodiments in which body 104 includes plural components, the components can be joined using an adhesive or by mechanical means, such as by using a snap fit or bayonet connection to list only a few possibilities.

As best seen in FIGS. 2-6, body 104 defines a hole 114 that extends through an approximate center of housing 102. More particularly, hole 114 extends from proximal end 116 through first portion 106 where it intersects and communicates cavity 118 defined by second portion 108. As described in greater detail below, hole 114 is sized such that it can receive a k-wire or other orthopedic device therein in a sliding manner. Cavity 118, in some embodiments, is sized and configured such that it can fit onto an end of a toe, finger, or other bodily appendage therein through open proximal end 120 as described in greater detail below.

Still referring to FIGS. 2, 3, 5, and 6, the interior 122 of first portion 106 includes a tapered slot 124 and a recess 126 in communication with slot 122. Slot 124 is formed such that it extends across and intersects hole 114 at an angle relative to a longitudinal axis of hole 114. The angle between the longitudinal axis defined by slot 122 and the longitudinal axis defined by hole 114 can vary as will be understood by one of ordinary skill in the art. In some embodiments, for example, the angle between longitudinal axis defined by slot 124 and the longitudinal axis defined by hole 114 is related to the diameter of a wire to be received within hole 114 and the diameter of hole 142 defined by locking clamp 132 described below. For example, the greater the difference between the two diameters, the greater the angle will be. Recess 126 can take a variety of shapes and is shown in FIGS. 2, 3, 5, and 6 as extending distally from slot 124. As described in greater detail below, recess 126 is sized and configured to receive a biasing mechanism 130, such as a compression spring, therein.

Figure 2:
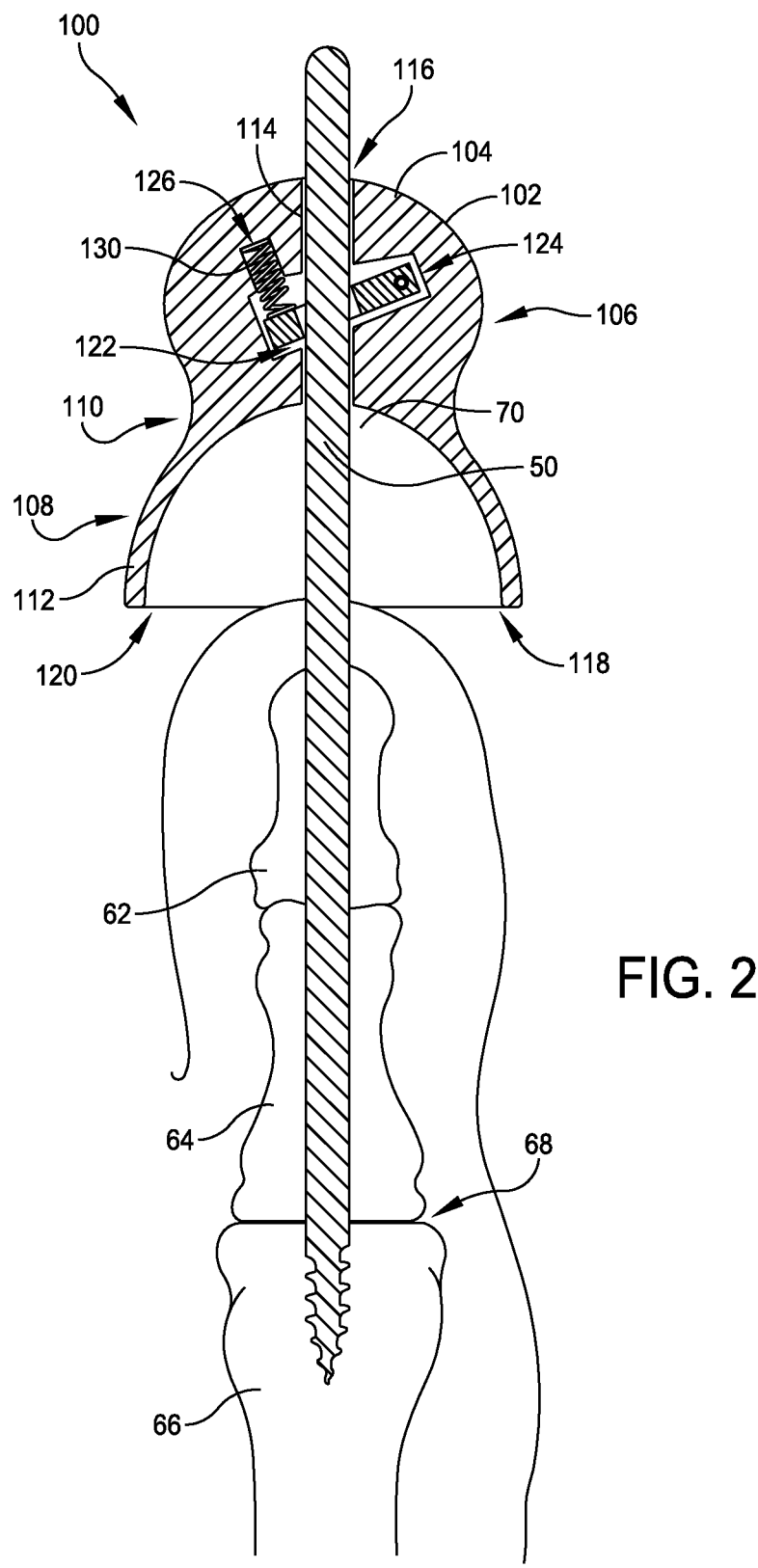
FIG. 2 is a cross-sectional view of a fixation device with an elongate orthopedic device disposed partially within a hole defined by the fixation device.
Figure 3:
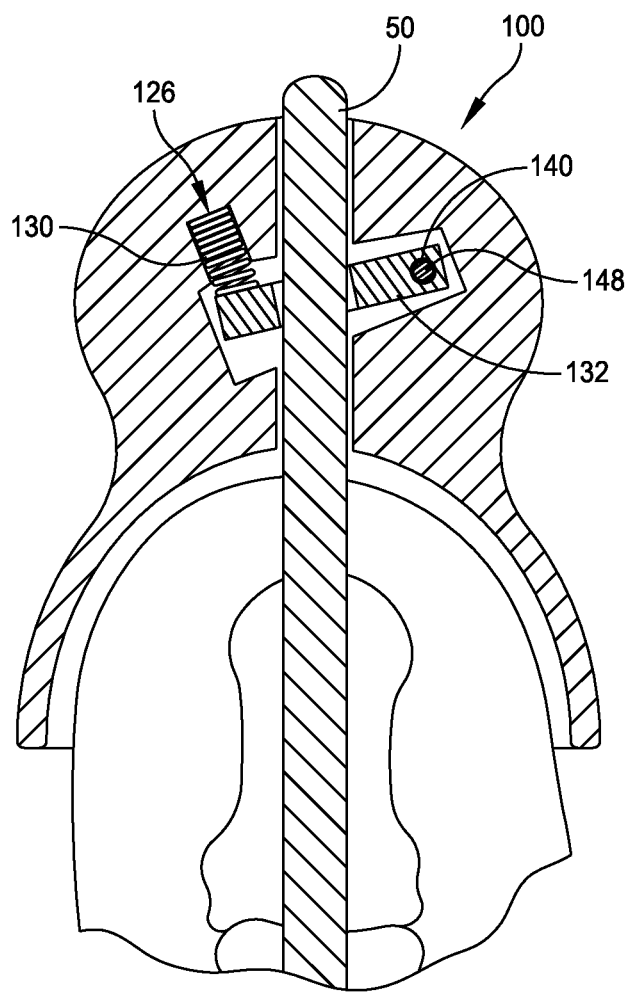
FIG. 3 is a cross-sectional view of a fixation device engaged with an elongate orthopedic device in accordance with some embodiments.
Figure 4:
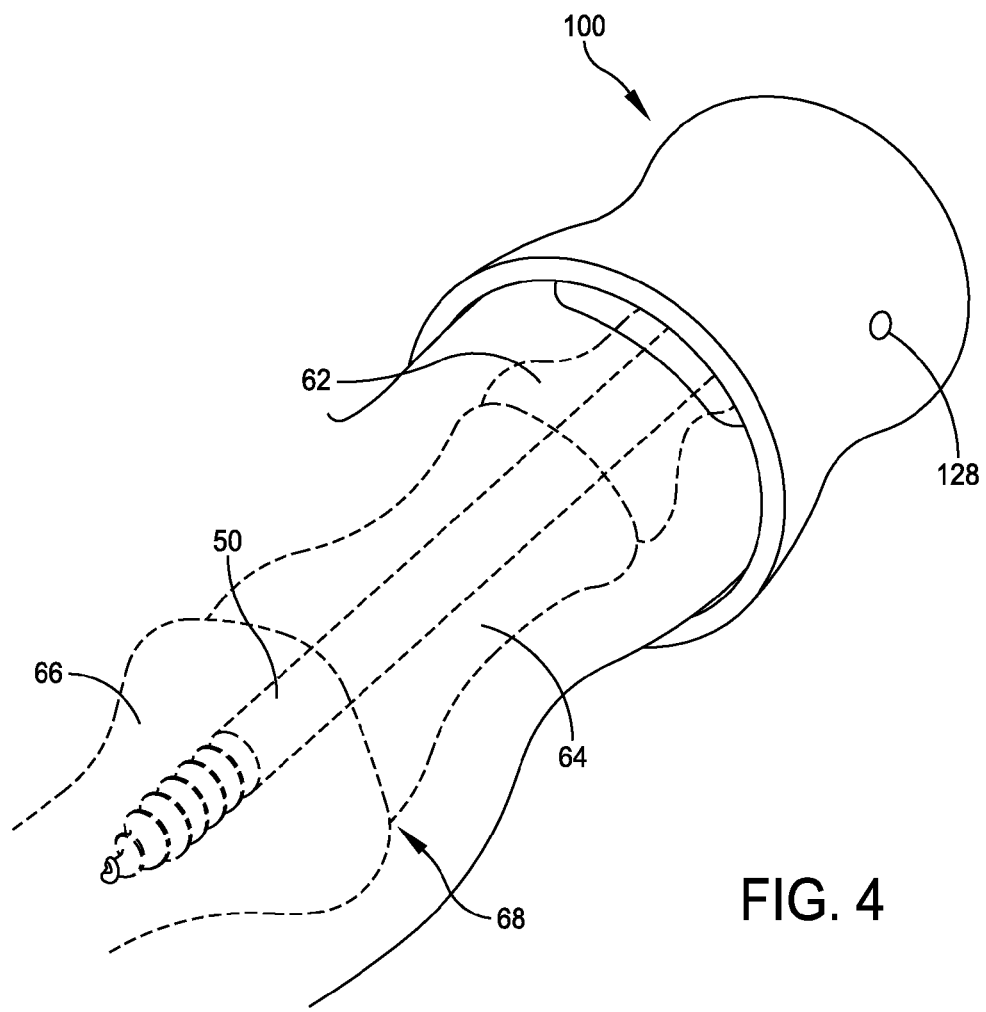
FIG. 4 is an isometric view of a fixation device disposed on an end of an extremity in accordance with some embodiments.
Figure 5:
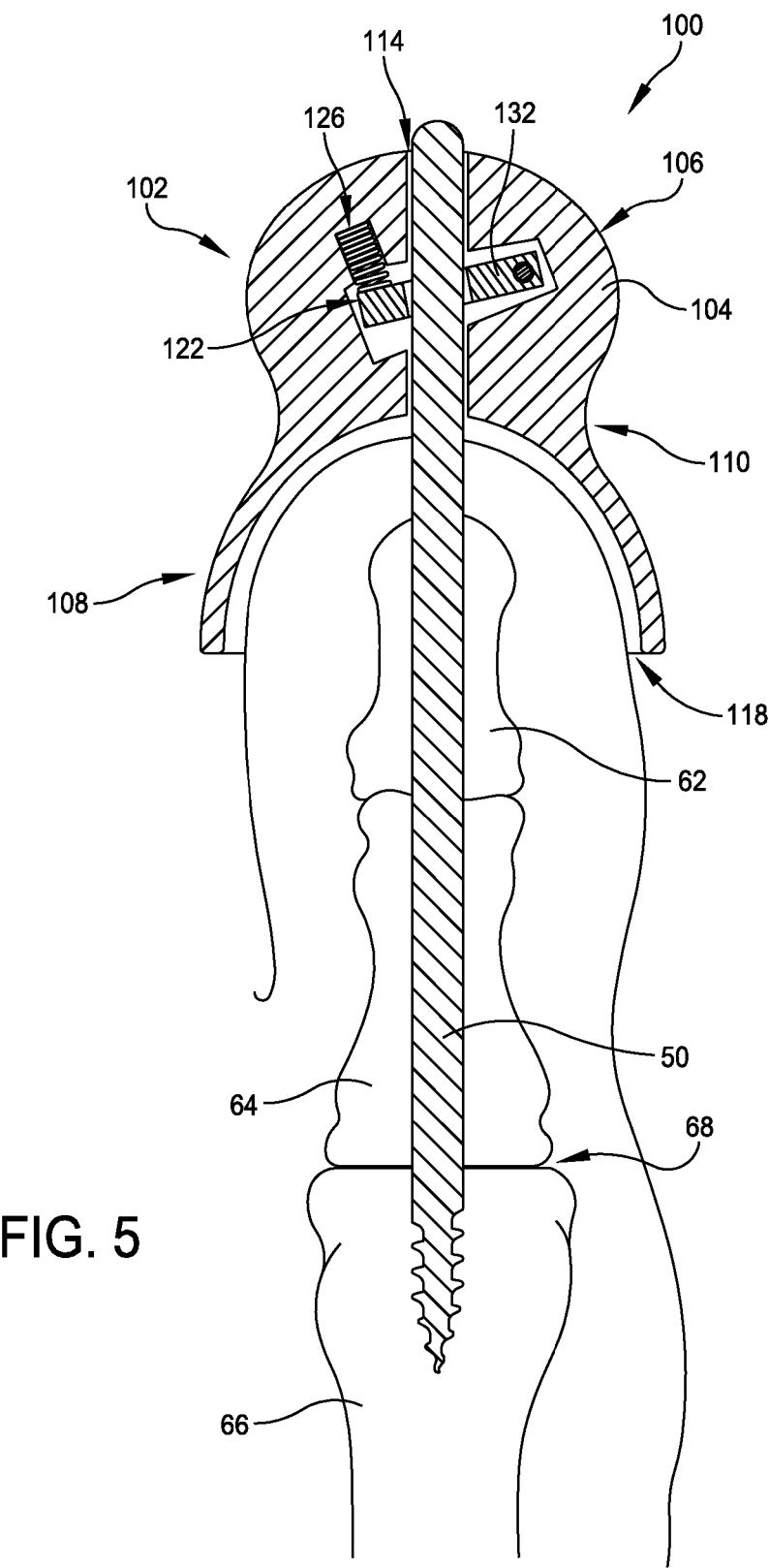
FIG. 5 is a cross-sectional view of an elongate fixation device inserted across several joints of an extremity with a fixation device disposed thereon in accordance with some embodiments.
Figure 6:
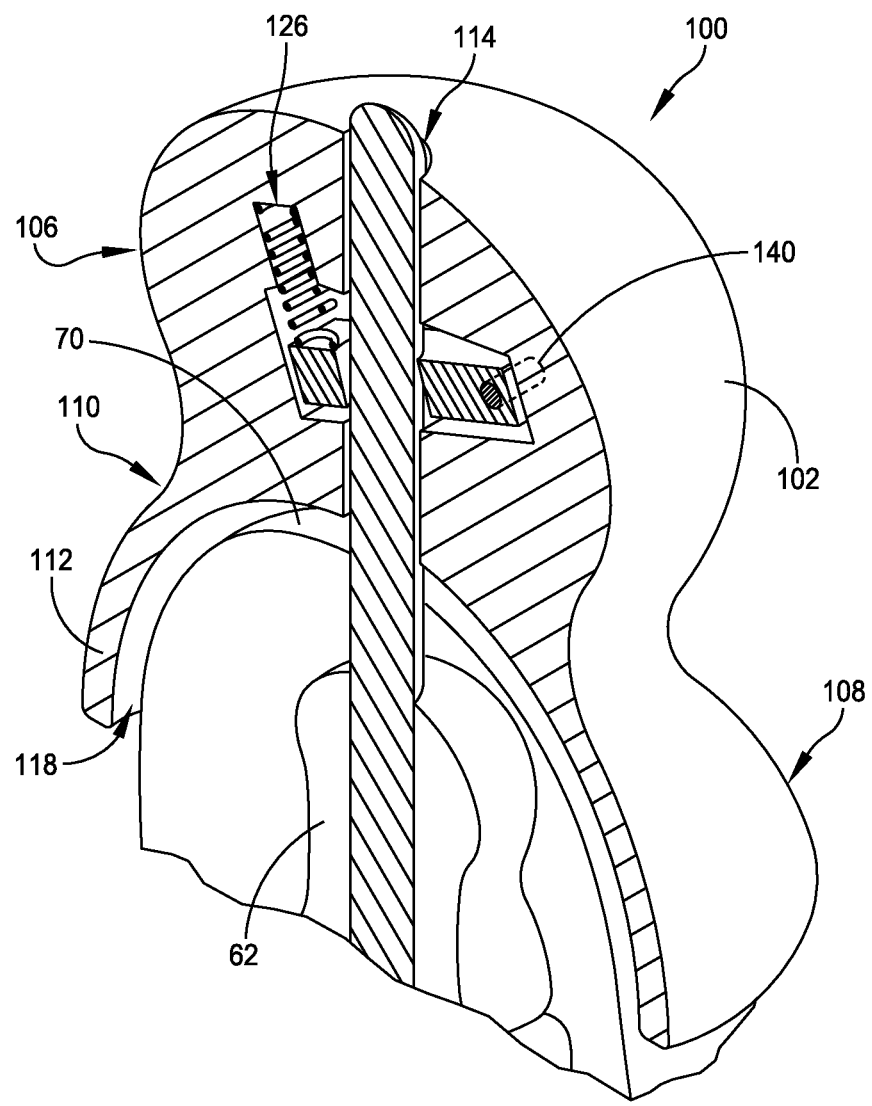
FIG. 6 is an isometric cross-sectional view of a fixation device engaged with an elongate orthopedic device in accordance with some embodiments.

Another hole 128 extends through first portion 106 in a direction that is perpendicular to a direction in which the locking clamp 132 extends as best seen in FIG. 4. As shown in FIGS. 2, 3, 5, and 6, hole 126 is offset from an approximate center of first portion 106 of housing 102 such that hole 126 does not intersect hole 114. In some embodiments, hole 126 is sized and configured to receive a pin therein.

Figure 2A:
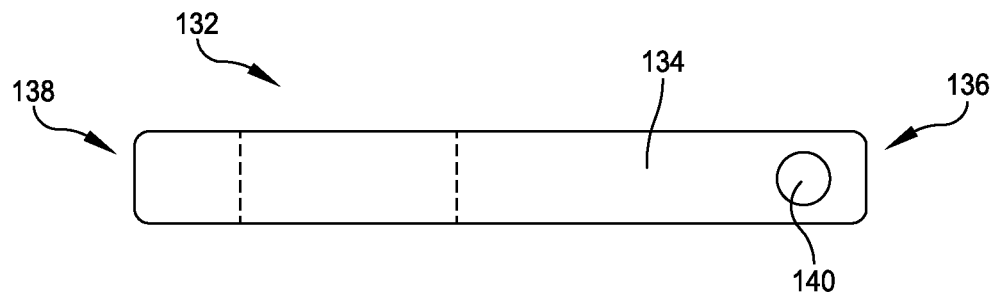
FIG. 2A is a side view of one example of a locking clamp in accordance with some embodiments.
Figure 2B:
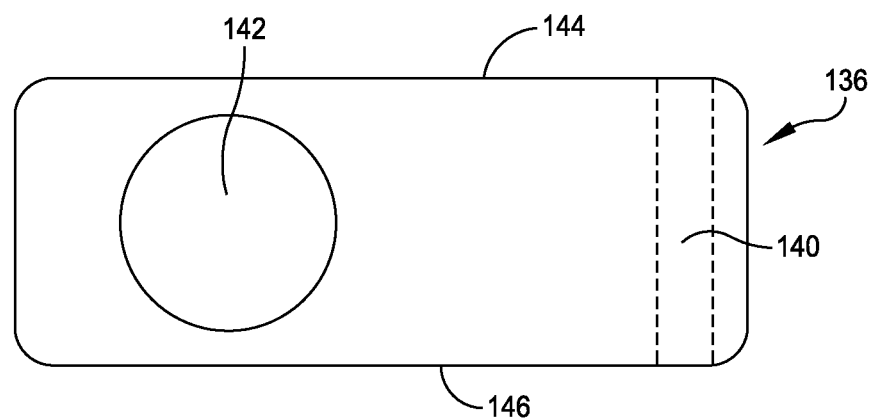
FIG. 2B is a top side plan view of the locking clamp illustrated in FIG. 2A in accordance with some embodiments.

Fixation system 100 also includes a locking assembly that, in some embodiments, includes a biasing mechanism 130 and a locking clamp 132. As best seen in FIGS. 2A and 2B, locking clamp 132 includes an elongate body 134 extending from a fixed end 136 to a free end 138. In some embodiments, elongate body 134 has a width dimension that is greater than a thickness dimension but less than a length dimension and defines a pair of spaced apart holes 140, 142. Hole 140 is disposed adjacent to fixed end 136 and is sized and configured to receive a pin therein for cross-pinning locking clamp 132 within housing 102. Hole 140 extends from a first side 144 to second side 146 such that hole 140 extends across the width dimension of elongate body 134.

Hole 142 is disposed adjacent to fixed end 136 at a distance from hole 140 and is sized and configured to receive a k-wire or other elongate orthopedic device therein. In some embodiments, hole 142 extends through elongate body 134 at a non-perpendicular angle with respect to a longitudinal direction of elongate body 134. However, one of ordinary skill in the art will understand that hole 142 can extend through elongate body 134 such that an axis defined by hole 142 is perpendicular to a longitudinal direction of elongate body 134. As shown in FIGS. 2A and 2B, hole 142 extends through elongate body 134 across the thickness dimension of elongate body 134.

Device 100 is assembled by placing biasing mechanism 130 in hole 126 defined by body 104 of housing 102, and locking clamp 132 is placed within slot 122 defined by body 104 of housing 102. A pin 148 is used to cross pin locking clamp 132 within slot 122 by aligning hole 140 defined by locking clamp 132 with hole 150 defined by body 104 of housing 102 and inserting pin 148 into holes 140 and 150.

One example of a method of using device 100 in connection with treating hammertoe is described with reference to FIGS. 1-6. However, one of ordinary skill in the art will understand that device 100 can be used in connection with numerous surgical procedures beyond the treatment of hammertoe as provided herein.

A k-wire, pin, or other elongate orthopedic device 50 is inserted into a distal end of a toe 60. For example, the orthopedic device 50 is inserted through the distal phalange 62 into a medial phalange 64 as shown in FIGS. 2-3. In some embodiments, orthopedic device 50 also is inserted into a proximal phalange 66 across the joint 68 between the medial phalange 64 and the proximal phalange 66.

With the orthopedic device 50 fully inserted into the toe 60, device 100 is slid over fixation device until it is placed into contact with toe 60 in FIGS. 2-6. For example, the proximal end of orthopedic device 50 is aligned with hole 114 formed within cavity 118 defined by second portion 108 of device 100 as best seen in FIG. 2. Device 100 is slid in a proximal direction, which results in distal end of orthopedic device 50 contacting locking clamp 132. When sufficient force is applied to device 100 to overcome the force of biasing mechanism 130, locking clamp 132 pivots about its pivot point, which in some embodiments is about a central axis defined by hole 140 formed in locking clamp 132.

Locking clamp 132 pivots until the distal end of orthopedic device 50 aligns with hole 142 such that fixation device is received within hole 142. Force continues to be applied such that device 100 slides along the length of orthopedic device 50 until the tip 70 of toe 60 is received within cavity 118 defined by the second portion 108 of device 100 and makes contact with body 104 of device 100.

With device 100 positioned along the length of orthopedic device 50, the extra length of orthopedic device 50, i.e., the length of orthopedic device 50 that extends from hole 114 at the distal end 116 of device, can be removed by cutting or snipping as will be understood by one of ordinary skill in the art. Device 100 advantageously continues to apply compression onto the tip 70 of toe 60 as device 100 is held in place along orthopedic device 50 due to biasing mechanism 130 pressing against locking clamp 132, which effectively locks device 100 to orthopedic device 50 by hindering device 100 from being moved proximally, i.e., away from tip 70 of toe 60.

When it is desired to remove orthopedic device 50 from toe 60, in some embodiments, device 100 is fractured using a surgical tool. For example, housing 102 of device 100 can be formed from a frangible material such as, for example, a rigid plastic. In some embodiments, housing 102 includes specific areas or lines that facilitate the breaking of housing 102. In some embodiments, an unlocking mechanism is provided that enables a user to reduce the friction between locking clamp 132 and orthopedic device 50. For example, the unlocking mechanism can include a pin or string that enables a user to pull locking clamp 132 in a distal direction to compress biasing mechanism 130 to reduce the engagement between locking clamp 132 and orthopedic device 50.

Figure 7:
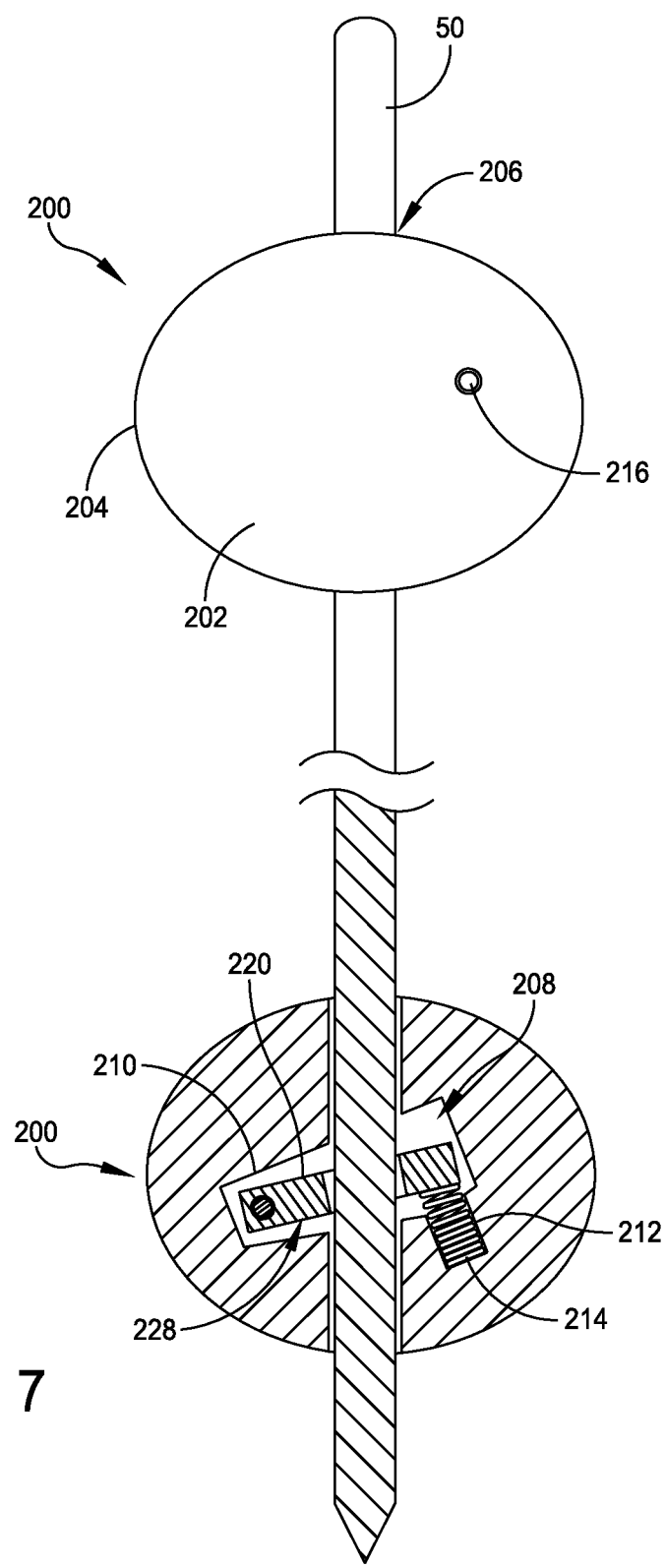
FIG. 7 illustrates one example of a pair of fixation devices—one shown in cross-section—disposed on an elongate orthopedic device in accordance with some embodiments.
Figure 8:
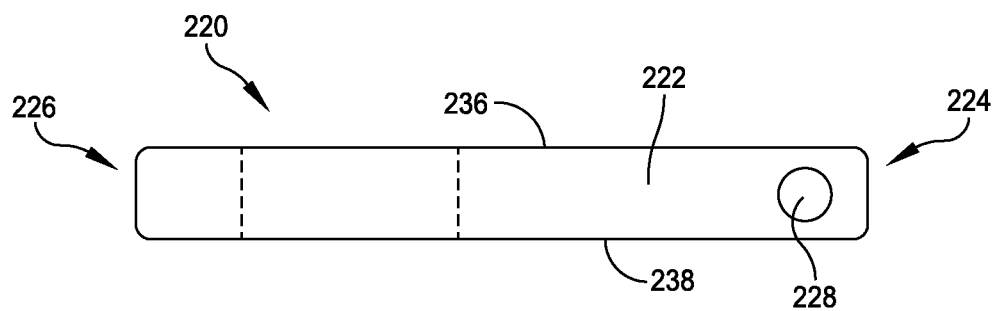
FIG. 8 is a side view of a locking clamp for use with a fixation device in accordance with the embodiment illustrated in FIG. 7.
Figure 9:
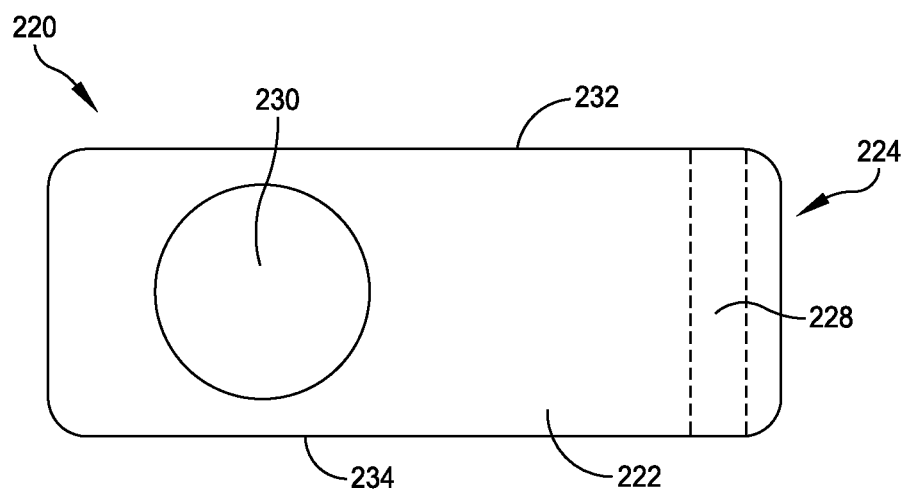
FIG. 9 is a top side plan view of the locking clamp illustrated in FIG. 8 in accordance with some embodiments.

The fixation devices disclosed herein can take a variety for forms. For example, FIGS. 7-9 illustrate another example of a fixation device 200 in accordance with some embodiments. As shown in FIG. 7, fixation device 200 includes a housing 202 having a generally spherical body 204. In some embodiments, body 204 is a monolith. In some embodiments, body 204 includes two or more components that are joined together such as by using an adhesive or a mechanical coupling. For example, in embodiments in which body 204 includes multiple components joint together using a mechanical coupling, the coupling can be one of a snap fit or bayonet connection to list only a few possibilities.

In some embodiments, body 204 defines a hole 206 that extends through an approximate center of housing 202. As described in greater detail below, hole 206 is sized such that it can receive a k-wire, pin, or other orthopedic device therein. Body 204 has an interior 208 that includes a tapered slot 210 and a recess 212 in communication with slot 210. Slot 210 intersects and extends across hole 206 that is formed through body 204. In some embodiments, slot 210 extends across hole 206 at a non-perpendicular angle. However, one of ordinary skill in the art will understand that slot 210 can extend across hole 206 at various angles, including perpendicular angles. Recess 212 can have a number of cross-sectional geometries. In some embodiments, recess 212 has a circular cross-sectional geometry and is sized and configured to receive a biasing mechanism 214 in the form a coil spring therein.

Housing 202 defines another hole 216 that extends through body 204 at a location that is offset from the center of body 204. Hole 216 is formed such that a longitudinal axis of hole 216 is approximately perpendicular to a longitudinal axis defined by hole 206. As described in greater detail below, hole 216 has a diameter that is sufficient to receive a pin for cross-pinning a locking clamp to housing 204.

The slot 210 and recess 212 are sized and configured to support a locking assembly, including a biasing mechanism 218 and locking clamp 220, therein. In some embodiments, locking clamp 220 is similar to locking clamp 132 in that locking clamp 220 has an elongate body 222 that extends from a fixed end 224 to a free end 226 as best seen in FIGS. 8 and 9. In some embodiments, body 222 of locking clamp 220 has a width dimension that is greater than a thickness dimension with both the thickness and width dimensions being less than the length dimension.

Still referring to FIGS. 8 and 9, body 222 defines a first hole 228 adjacent to fixed end 224, and a second hole 230 is defined along the length of body 222 closer to free end 238. Hole 228 extends through body 222 from a first side 232 to a second side 234 in a widthwise direction. Hole 230 extends from an upper side 236 to a bottom side 238. In some embodiments, hole 230 extends through body 222 at a non-perpendicular angle with respect to a plane defined by one of the upper side 236 or the bottom side 238. One of ordinary skill in the art will understand that hole 230 can extend through body perpendicularly with respect to a plane defined by the upper side 236 or the bottom side 238.

Fixation device 200 can be assembled by inserting locking assembly into the internal space provided by slot 210 and recess 212. For example, biasing mechanism 214 is placed within recess 212, and locking clamp 220 is placed within slot 210. To secure locking clamp 220 within slot 210, hole 228 defined by the body 222 of locking clamp 220 is aligned with hole 216 defined by body 204 of housing 202. With holes 216 and 228 aligned, a pin 236 is inserted into holes 216 and 228 to secure locking clamp 220 to housing 202.

Fixation device 200 can be used in a number of ways. For example, in some embodiments, plural fixation device 200 are used to provide compression to a body part of a patient, such as shown in FIG. 7. One of ordinary skill in the art will understand that the following description represents only one possible example of using one or more fixation devices 200.

In some embodiments, a k-wire, pin, or other elongate orthopedic device 50 is inserted into and across one or more bones. For example, orthopedic device 50 can be inserted across, i.e., in the medial-lateral direction, a patient's foot, hand, or other extremity until at least a portion of orthopedic device 50 is accessible on either side of the foot, hand, or extremity.

A first fixation device 200 is slid onto a first accessible portion of the orthopedic device 50, such as the portion extending from the medial side of the extremity. In some embodiments, hole 206 of device 200 is aligned with orthopedic device 50, and orthopedic device 50 is received within hole 206. Device 200 is urged proximally, i.e., towards the extremity, which results in an end of orthopedic device 50 contacts a side 240 of locking clamp 220. A user continues to apply force to fixation device 200 causing locking clamp 220 to pivot about its pivot point, i.e., the central axis defined by hole 228. As locking clamp 220 pivots, the end of orthopedic device 50 slides along side 240 of locking clamp 220 until the end of orthopedic device 50 is received within hole 230 defined by locking clamp 220.

With device 50 positioned within hole 230, the user continues to move fixation device 200 along orthopedic device 50 until the body 204 of fixation device 200 contacts the extremity. Once fixation device 200 is positioned along the length of fixation device 50 and contacts the patient's extremity, any portion of orthopedic device 50 that extends beyond fixation device 200 can be removed by cutting or snipping as will be understood by a person of ordinary skill in the art.

In some embodiments, a second fixation device 200 is placed on the opposite end of the orthopedic device 50, i.e., the end of orthopedic device 50 extending from the lateral side of the patient's extremity. The manner in which the second fixation device 200 is placed on the lateral side is the same as the manner in which the first fixation device 200 is placed on the medial side.

The use of plural fixation devices 200 advantageously provides a compressive fixation system using few relatively inexpensive components. Due to the biting action of the locking assembly, i.e., the combination of biasing mechanism 218 and locking clamp 220, on orthopedic device 50, fixation devices 200 continue to provide compression to the patient's extremity. Put another way, fixation device 200 are locked in the position at which the user places them along orthopedic device 50 and maintain the compression applied by the user when placing the devices 200 along orthopedic device 50.

When it is desired to remove orthopedic device 50 from the patient's extremity, devices 200 are fractured using a surgical tool in some embodiments. For example, housing 202 of devices 200 can be configured to be frangible, such as by fabricating housing 202 from a frangible material, e.g., a rigid polymer. In some embodiments, housing 202 includes areas or lines that facilitate the breaking of housing 202.

Additionally or alternatively, devices 200 are configured with an unlocking mechanism in some embodiments. For example, the unlocking mechanism enables a user to reduce the friction between locking clamp 220 and orthopedic device 50 and includes a pin or string that enables a user to pull locking clamp 200 in a proximal direction to compress biasing mechanism 218 to reduce the engagement between locking clamp 220 and orthopedic device 50.

Fixation devices 100, 200 can be packaged together as a kit in which a plurality of different fixation devices 100, 200 are placed in a sterilized packaged along with a plurality of other devices, including one or more elongate orthopedic devices. In some embodiments, a kit includes only a number of fixation devices 100 or fixation devices 200 and are not providing together in a single hermetically sealed package.

Although the devices, systems, kits, and methods have been described in terms of exemplary embodiments, they are not limited thereto. Rather, the appended claims should be construed broadly, to include other variants and embodiments of the devices, systems, kits, and methods, which may be made by those skilled in the art without departing from the scope and range of equivalents of the devices, systems, kits, and methods.

What is claimed is:

1. A device, comprising:
   a housing including a first portion having a spherical shape and a second portion coupled to the first portion at an intersection, the second portion including a hollow cylindrical wall extending away from the intersection, wherein the hollow cylindrical wall defines an opening sized to receive at least a portion of a digit of a patient therein, the housing further defining a first hole and a second hole, the first hole extending through the housing and defining a first axis, and the second hole extending through the housing and defining a second axis that is not parallel to the first axis; and
   a locking assembly disposed within a space defined by the housing, the locking assembly including a locking clamp disposed within a slot defined by the housing and extending across the first hole defined by the housing, the locking clamp pivotally coupled to the housing by a pin that is received through the second hole defined by the housing and through a third hole defined by the locking clamp,
   wherein the locking assembly is configured to allow the device to slide along an elongate orthopedic device in a first direction and to hinder sliding in a second direction that is opposite the first direction.

2. The device of claim 1, wherein the locking assembly includes
   a biasing mechanism disposed within a recess defined by the housing.

3. The device of claim 2, wherein the biasing mechanism includes a compression spring.

4. The device of claim 1, wherein the locking clamp defines a fourth hole that is positioned along a body of the locking clamp such that it at least partially aligns with the first hole defined by the housing.

5. A method, comprising:
   inserting an elongate orthopedic device into at least one bone of a patient, wherein inserting the elongate orthopedic device into at least one bone of the patient includes inserting the elongate orthopedic device into a plurality of bones of an extremity of the patient until a leading end of the elongate orthopedic device emerges from the extremity; and
   sliding a first fixation device along a length of the elongate orthopedic device such that the elongate orthopedic device is received within a first hole defined by a housing of the first fixation device, the first fixation device including a locking assembly disposed within a space defined by the housing, the locking assembly including a locking clamp disposed within a slot defined by the housing and extending across the first hole defined by the housing, the locking clamp pivotally coupled to the housing by a pin that is received through a second hole defined by the housing and through a third hole defined by the locking clamp, the second hole extending through the housing and defining a second axis that is not parallel to a first axis defined by the first hole;
   sliding a second fixation device along a length of the elongate orthopedic device such that the elongate orthopedic device is received within a hole defined by a housing of the second fixation device; and
   wherein the locking assembly of the first fixation device is configured to allow the first fixation device to slide along the elongate orthopedic device in a first direction and to hinder sliding in a second direction that is opposite the first direction.

6. The method of claim 5, further comprising removing a portion of the elongate orthopedic device that extends from the first fixation device.

7. The method of claim 5, wherein the locking assembly of the first fixation device includes
   a biasing mechanism disposed within a recess defined by the housing of the first fixation device.

8. The method of claim 7, wherein the elongate orthopedic device is received within a fourth hole defined by the locking clamp of the first fixation device as the first fixation device slides along the length of the elongate orthopedic device.

9. The method of claim 8, wherein the biasing mechanism presses against a body of the locking clamp when the elongate orthopedic device is received within the fourth hole defined by the locking clamp of the first fixation device to hinder the first fixation device from sliding along the elongate orthopedic device in the second direction.

10. The method of claim 9, wherein the biasing mechanism includes a compression spring.

11. The method of claim 5 wherein the second fixation device includes a locking assembly disposed within a space defined by the housing, and wherein the locking assembly of the second fixation device is configured to allow the second fixation device to slide along the elongate orthopedic device in the second direction and to hinder sliding in first direction that is opposite the second direction.

12. The method of claim 5, wherein the housing of the first fixation device includes
   a first portion having a spherical shape; and
   a second portion coupled to the first portion at an intersection, the second portion including a hollow cylindrical wall extending away from the intersection.

13. The method of claim 12, wherein the first fixation device is slid along the elongate orthopedic device until a portion of an extremity of the patient contacts the hollow cylindrical wall.

14. The method of claim 12, wherein the extremity is a toe.

15. A method, comprising:
   inserting an elongate orthopedic device into at least one bone of a patient;
   sliding a first fixation device along a length of the elongate orthopedic device such that the elongate orthopedic device is received within a first hole defined by a housing of the first fixation device, the first fixation device including a locking assembly disposed within a space defined by the housing; and
   sliding a second fixation device along a length of the elongate orthopedic device such that the elongate orthopedic device is received within a hole defined by a housing of the second fixation device,
   wherein the locking assembly of the first fixation device is configured to allow the first fixation device to slide along the elongate orthopedic device in a first direction and to hinder sliding in a second direction that is opposite the first direction.

* * * * *